US00RE35218E

United States Patent [19]

Becker et al.

[11] E Patent Number: Re. 35,218

[45] Reissued Date of Patent: Apr. 23, 1996

[54] AZATETRACYCLE COMPOUNDS

[75] Inventors: Daniel P. Becker, Glenview; Daniel L. Flynn, Mundelein; Roger Nosal, Buffalo Grove; Dale P. Spangler, Deerfield, all of Ill.; Daniel L. Zabrowski, Pleasanton, Calif.

[73] Assignee: G. D. Searle & Co., Chicago, Ill.

[21] Appl. No.: 292,894

[22] Filed: Aug. 18, 1994

Related U.S. Patent Documents

Reissue of:

[64] Patent No.: 5,140,023
Issued: Aug. 18, 1992
Appl. No.: 682,993
Filed: Apr. 12, 1991

U.S. Applications:

[63] Continuation-in-part of Ser. No. 515,391, Apr. 27, 1990, abandoned.

[51] Int. Cl.[6] ..... A61K 31/395; C07D 451/00; C07D 451/02; C07D 451/14

[52] U.S. Cl. ..... 514/214; 514/294; 540/581; 546/94

[58] Field of Search ..... 546/94; 540/581; 514/214, 294

[56] References Cited

U.S. PATENT DOCUMENTS

| | | | |
|---|---|---|---|
| 4,273,778 | 6/1981 | Hadley et al. | 424/265 |
| 4,336,259 | 6/1982 | Hadley et al. | 424/265 |
| 4,797,387 | 1/1989 | King | 514/212 |
| 4,797,406 | 1/1989 | Richardson et al. | 514/299 |
| 4,816,453 | 3/1989 | Watts | 514/217 |

FOREIGN PATENT DOCUMENTS

| | | |
|---|---|---|
| 0012496 | 9/1983 | Australia . |
| 0067121 | 7/1987 | Australia . |
| 0076592 | 4/1983 | European Pat. Off. . |
| 0094742 | 11/1983 | European Pat. Off. . |
| 0189002 | 7/1986 | European Pat. Off. . |
| 0201165 | 11/1986 | European Pat. Off. . |
| 0220011 | 4/1987 | European Pat. Off. . |
| 0230718 | 6/1987 | European Pat. Off. . |
| 0315390 | 5/1989 | European Pat. Off. . |
| 2152049 | 7/1985 | United Kingdom . |
| 2166729 | 5/1986 | United Kingdom . |
| 2166726 | 5/1986 | United Kingdom . |
| 2169292 | 7/1986 | United Kingdom . |

OTHER PUBLICATIONS

Fludzinski et al, "Imidazoles As Indole Bioisosteres", J. Med. Chem., vol. 30, No. 9, pp. 1535–1537 (1987).

*Primary Examiner*—Floyd D. Higel
*Attorney, Agent, or Firm*—Cynthia S. Kovacevic; Roger A. Williams

[57] ABSTRACT

An azatetracycle compound useful as $5HT_3$ antagonists of the general formula $$Ar+A-\overset{\overset{O}{\|}}{C}-B\frac{}{p}D$$

wherein D is a tetracycle of the structure

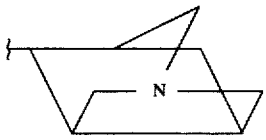

or

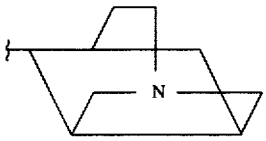

wherein Ar is an aromatic moiety and B is either NH or O.

52 Claims, No Drawings

AZATETRACYCLE COMPOUNDS

Matter enclosed in heavy brackets [ ] appears in the original patent but forms no part of this reissue specification; matter printed in italics indicates the additions made by reissue.

This application is a *reissue of Ser. No. 07/682,993 filed Apr. 12, 1991, now U.S. Pat. No. 5,140,023 which is a* continuation-in-part of U.S. patent application Ser. No. 07/515,391 filed Apr. 27, 1990, now abandoned.

BACKGROUND OF THE INVENTION

The invention herein is directed to azatetracycle compounds of the general formula

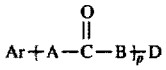

wherein A can be NH or a covalent bond, wherein p can be 1 or 0, Ar represents an aromatic moiety as will hereinafter be further discussed, B represents NH or O and D represents the tetracyclic structure

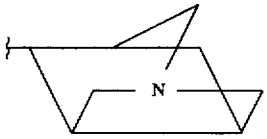

or

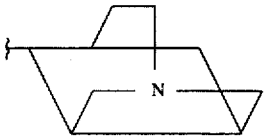

or

The azatetracylic compounds of the present invention are useful in the treatment of gastrointestinal motility disorders such as gastroesophageal reflux, non-ulcer dyspepsia, delayed gastric emptying, ileus, irritable bowel syndrome, and the like. Further, the compounds of the present invention exhibit 5-$HT_3$ antagonist activity making the compounds useful as 5-$HT_3$ antagonists. The compounds are therefore useful as antiemetics, analgesics, anxiolytics, and exhibit utility in the treatment of substance abuse, schizophrenia, depression, and migraine headaches, presenile and senile dementia (i.e., Alzheimer's disease and senile dementia of the Alzheimer type), and enhancers of intra-nasal absorption of bioactive compounds.

Aza-adamantyl compounds are disclosed in U.S. Pat. No. 4,816,453 and are mentioned generically in: U.K. Patent 2,152,049A; European application 0189002A2; and U.K. Patent 21,169,292B.

Azabicyclic nonanes are disclosed in European Patent application 0094742A2. Additional azabicyclic compounds are disclosed in: U.S. Pat. No. 4,797,387; European application 323,077A; European Patent 0230718A1; J. Med. Chem. (1987) 30,1535; Australian Patent 8767121; European Patent 0094742A2; Australian Patent 8207867; and European Patent 031539082. In addition general azabicyclic systems are disclosed in the following Patents: European Patent 0076592A2; U.K. Patent 2166726A; European Patent 0201165A2; European Patent 0220011A2; U.S. Pat. Nos. 4,336,259; 4,273,778; and 4,797,406.

SUMMARY OF THE INVENTION

The invention herein is directed to azatetracyclic compounds of the general formula

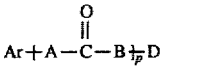

wherein D can be

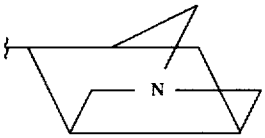

or

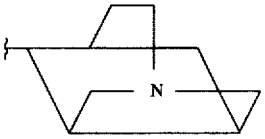

wherein B can be NH or O;
wherein A can be NH or a bond;
wherein p can be 1 or 0; and
when p is 1, Ar can be

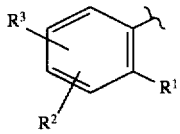

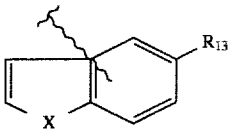

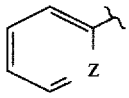

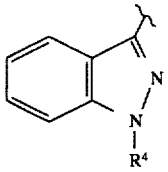

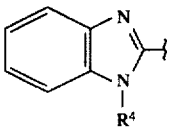

and when p is 0, Ar can be

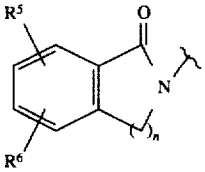

-continued

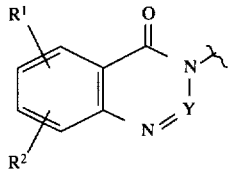

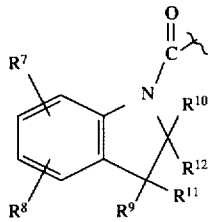

wherein X can be O,S,N,($R^4$) or $CH_2$;
wherein Y can be N or CH;
wherein n is 1 or 2;
wherein Z can be

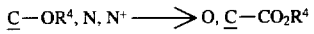

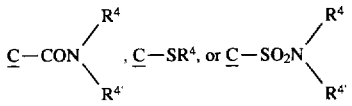

wherein $R^1$ can be alkoxy of 1 to 6 carbon atoms;
wherein $R^2$ and $R^3$ are the same or different and can be hydrogen, halogen, $CF_3$, hydroxyl, $C_{1-2}$ alkoxy, $C_{2-7}$ acyl, amino, amino substituted by one or two $C_{1-6}$ alkyl groups, $C_{2-7}$ acyl amino, amino carbonyl, or amino sulfone optionally substituted by one or two $C_{1-6}$ alkyl groups, $C_{1-6}$ alkyl sulfone or nitro groups;

wherein $R^4$ and $R^{4'}$ can be the same or different and can be hydrogen, alkyl or arylalkyl;
wherein $R^5$ and $R^6$ can be the same or different and can be hydrogen, halogen, $CF_3$, $C_{1-6}$ alkyl, $C_{1-7}$ acyl, $C_{1-7}$ acylamino, or amino, amino carbonyl or amino sulfonyl, optionally substituted by one or two $C_{1-6}$ alkyl or $C_{3-8}$ cycloalkyl groups, or by $C_{4-5}$ polymethylene or biphenyl, $C_{1-6}$ alkylsulfonyl, $C_{1-6}$ alkylsulfinyl, $C_{1-6}$ alkoxy, $C_{1-6}$ alkylthio, hydroxy or nitro or when $R^5$ and $R^6$ are taken together are methylenedioxy or ethylenedioxy;
wherein $R^9$ and $R^{10}$ can be the same or different and can be hydrogen, $C_{1-6}$ alkyl, $C_{2-6}$ alkenyl, $C_{2-4}$ alkynyl or together are $C_{2-4}$ polymethylene;
wherein $R^7$ and $R^8$ are the same or different and can be hydrogen, halogen, $CF_3$, $C_{1-6}$ alkyl, $C_{1-6}$ alkoxy, $C_{1-6}$ alkylthio, $C_{1-7}$ acyl, $C_{1-7}$ acylamino, $C_{1-6}$ alkylsulfonylamino, N-($C_{1-6}$ alkylsulfonyl)-N-$C_{1-4}$ alkylamino, $C_{1-6}$ alkylsulfinyl, hydroxy, nitro or amino, aminocarbonyl, aminosulfonyl, aminosulfonylamino or N'-(aminosulfonyl)-$C_{1-4}$ alkylamino optionally N-substituted by one or two groups selected from $C_{1-6}$ alkyl, $C_{3-8}$ cycloalkyl, phenyl, or phenyl $C_{1-4}$ alkyl groups or Optionally N'-disubstituted by $C_{4-5}$ polymethylene; and
wherein $R^{11}$ and $R^{12}$ can be the same or different and can be hydrogen or $C_{1-4}$ alkyl or taken together are a covalent bond and $R^{13}$ can be H, halogen or $OR^4$.

DETAILED DESCRIPTION

The azatetracyclic compounds that are the subject of the invention herein can be prepared in the following reaction Schemes I and II. In reaction Scheme I a method of producing azatetracyclic benzamides is shown and in reaction Scheme II a method for producing azatetracyclic amines is shown.

Scheme I

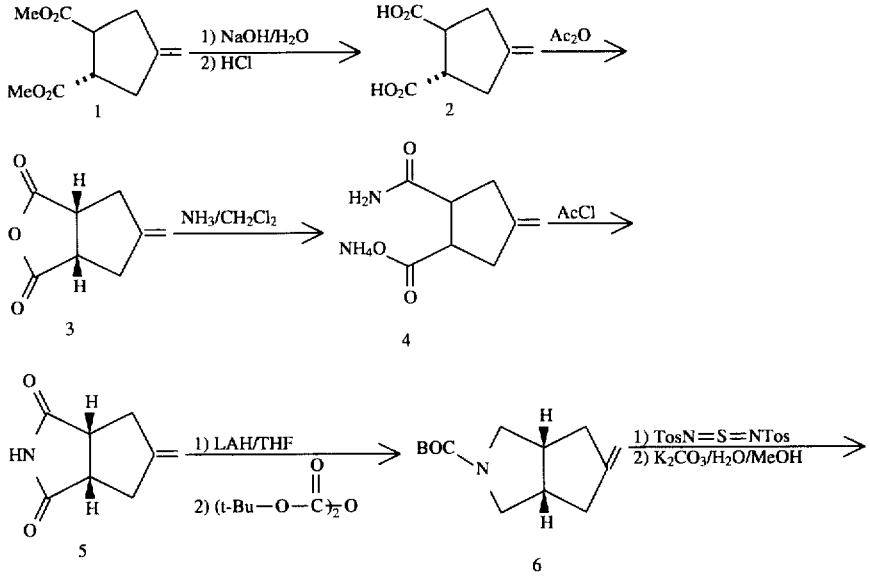

-continued

Scheme I

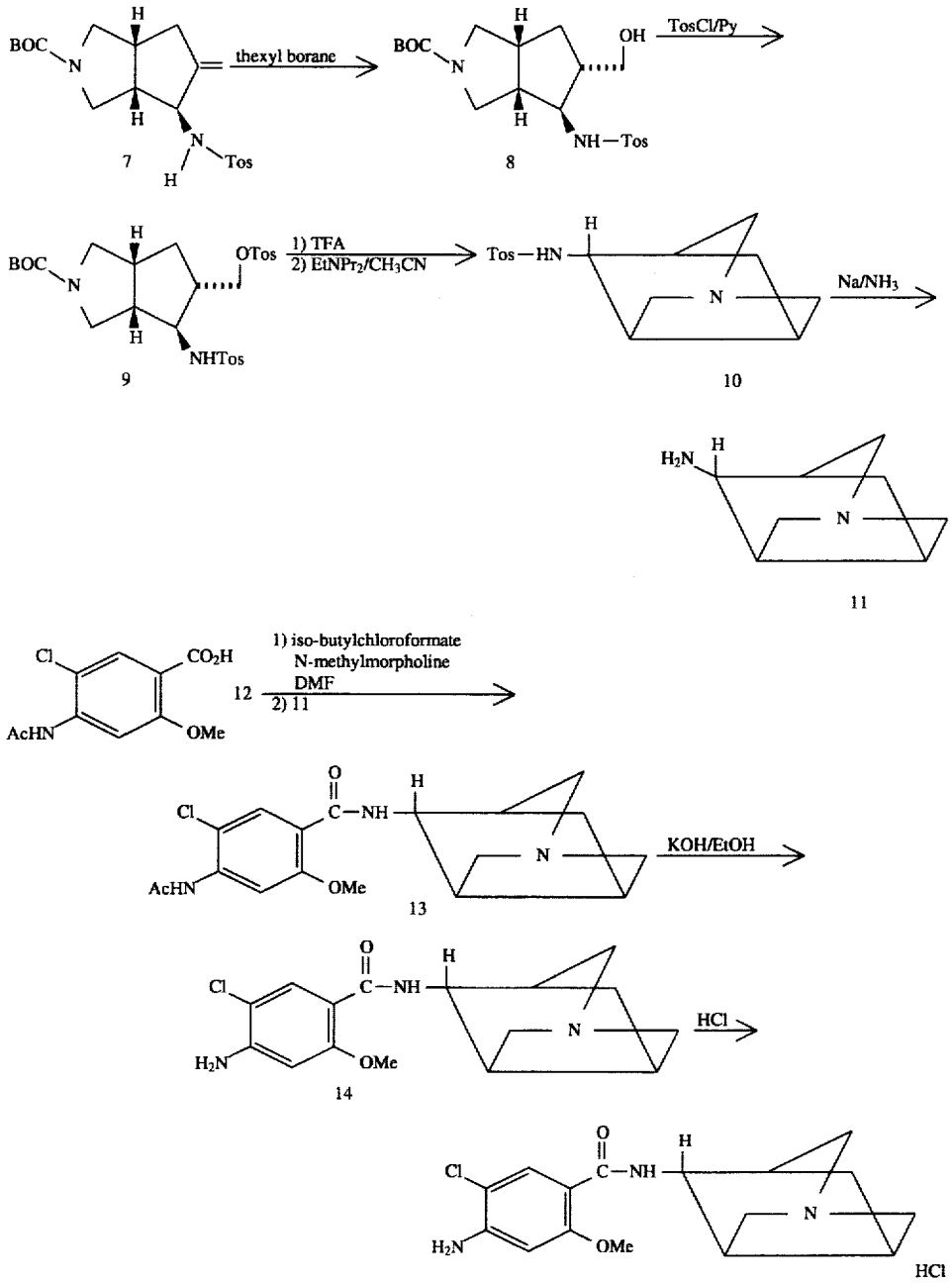

Referring to reaction Scheme I, trans-1,2-di-carbomethoxy-4-methylene-cyclopentane is reacted with sodium hydroxide followed with acid to produce trans-4-methylene-1,2-cyclopentanedicarboxylic acid. The dicarboxylic acid is reacted with acetic anhydride to produce cis-tetrahydro-5-methylene- 1H-cyclopenta[c]furan-1,3(3aH)-dione. The ammonium salt 4 is prepared by reacting the anhydride 3 in dry methylene chloride with ammonia gas. The imide 5 is prepared from the ammonium salt by reacting the ammonium salt with acetyl chloride. The imide is reacted with lithium aluminum hydride and ditertiarybutyl dicarbonate to produce cis-1,1-dimethylethylhexahydro-5-methylenecyclopenta[ c]pyrrole-2(1H)carboxylate 6. The term BOC is used herein to refer to t-butyloxy carbonyl. The BOC-amine 6 is reacted with bis(p-toluenesulfonyl) sulfodiimide to produce the p-toluenesulfonamide 7. The term Tos is used herein to represent p-toluenesulfonyl. The p-toluenesulfonamide is reacted with thexyl borane to produce the endo alcohol 8. The endo alcohol is reacted with p-toluenesulfonyl chloride to produce the tosylate 9. The tosylate 9 is reacted with trifluoroacetic acid and treated with Hunig's base to provide the p-toluenesulfonamide tetracycle 10. The sulfonamide tetracycle 10 was reductively cleaved to produce the aminoazatetracycle 11. Coupling of the aminoazatetracycle 11 with benzoic acid derivative 12 under mixed anhydride conditions gave the protected benzamide tetracycle 13. Basic hydrolysis of the acetamide 13 gives the benzamide tetracycle 14 which upon treatment with HCl produces the hydrochloride salt of the benzamide tetracycle 15.

A more detailed description of the process shown in Scheme I is set forth in the following Examples 1–12.

EXAMPLE 1 trans-4-methylene-1,2-cyclopentanedicarboxylic acid 2

A diester, trans-1,2-di-carbomethoxy-4-methylenecyclopentane, (1.48g, 7.47 mmol) prepared by the method of Trost (J. Am. Chem. Soc. 105 2315 (1983) was heated under reflux for 2 hours with 2N sodium hydroxide (11 ml, 22 mmol). The resulting solution was cooled in an ice bath and acidified with concentrated (37%) hydrochloric acid (8.0 ml) until a pH of 0.6 was attained. The resulting slurry was filtered, washed with water, and dried in vacuo to give the diacid 2 (0.987g, 77.7%) as a colorless powder: mp 178°–179° C.; Anal. calcd for $C_8H_{10}O_4$: C, 56.47; H, 5.92. Found: C, 56.08; H, 5.87.

EXAMPLE 2 cis-tetrahydro-5-methylene-1H-cyclopenta[c]furan-1,3(3aH)-dione 3

A suspension of the diacid 2 (689 mg, 4.05 mmol) from Example 1 in freshly distilled acetic anhydride (7 ml) was heated for 4 hours at 100° C. The majority of acetic anhydride was removed by distillation and the remainder was removed under a stream of nitrogen leaving a residue which was distilled (170°–175° C. at 1 mm Hg) giving the desired anhydride 3 (175 mg, 28%) as an oil which crystallized on standing: mp 50°–51° C.; Anal. calcd for $C_8H_8O_3$: C, 63.15; H, 5.30. Found: C, 62.91; H, 5.43.

EXAMPLE 3 cis-4-methylene-2-carboxamidocyclopentane-1-carboxylic acid, ammonium salt

Into a solution of anhydride 3 from Example 2 (14.6 g, 95.9 mmol) in chloroform (900 ml) was bubbled ammonia gas for 2 hours. The resulting suspension was filtered, washed with chloroform and dried to give the ammonium salt 4 (11.64 g, 65.2%) as a colorless powder: mp 158°– 160° C. (dec); Anal. calcd for $C_8H_{14}N_2O_3$: C, 51.60; H, 7.58; N, 15.04. Found: C, 51.45; H,7.51; N, 14.79.

EXAMPLE 4 cis-tetrahydro-5-methylenecyclopenta[c]pyrrole-1,3(2H,3aH)-dione 5

A suspension of ammonium salt 4 from Example 3 (2.18g, 11.7 mmol) in freshly distilled acetyl chloride (40 ml) was heated under reflux for 22 hours. The resulting solution was concentrated under a stream of nitrogen, then in vacuo, to give a dark oil which was dissolved in methanol (10 ml) and treated with ammonia-saturated methanol (10 ml) and stirred for 3.5 hours. The solution was concentrated under a stream of nitrogen to give an oil which was chromatographed on silica gel eluting with ethanol/methylene chloride (1/99, then 2/98) to give the imide 5 (1.46g, 82.6%) as a colorless solid which was recrystallized from chloroform/hexane to give the desired imide 5 (1.21g) as colorless needles; mp 135°–137° C. (softens at 133° C.). Anal. calcd for $C_8H_9NO_2$: C, 63.56; H, 6.00; N, 9.27. Found: C, 63.60; H, 6.03; N, 9.12.

EXAMPLE 5 cis-1,1-dimethylethylhexahydro-5-methylenecyclopenta[c] pyrrole-2(1H)-carboxylate (BOC amine 6)

To a solution of lithium aluminum hydride (11.8 ml of a 1M solution in THF) was added a solution of the imide 5 from Example 4 (1.19g, 7.89 mmol) in dry THF (26 ml) dropwise via syringe. After the addition was complete the reaction was stirred for 1½ hours at room temperature, then heated under reflux for 2 hours. After cooling to room temperature the reaction was quenched with the addition of 0.45 ml $H_2O$ followed by the addition of 0.45 ml of 15% NaOH then 1.35 ml of $H_2O$. The solids were removed by filtration and rinsed with dry THF (11×10 ml) giving a solution which was treated immediately with di-tert-butyl dicarbonate (1.89 g, 8.68 mmol). The solution was stirred under argon for 5 days at room temperature and concentrated under a stream of nitrogen to give an oil which was purified by chromatography eluting with ethyl acetate/hexane (5/95, then 10/90) to give the desired BOC amine 6 (1.34 g, 76%) as a colorless oil: Anal. calcd for $C_{13}H_{21}NO_2$: C, 69.92; H 9.48; N, 6.27. Found: C, 69.03; H, 9.47; N, 6.20 Ms: calcd for $C_{13}H_{21}NO_2$, 223.1572; Found, 223.1578.

EXAMPLE 6

1,1-dimethylethylhexahydro-5-methylene-4β-[[(4-methylphenyl)sulfonyl]amino]-3aβ, 6aβ-cyclopenta[c]pyrrole-2(1H)-carboxylate (p-toluenesulfonamide 7)

To a solution of the BOC amine 6 (78.4 mg, 0.35 mmol) from Example 5 in dry dichloromethane (2 ml) was added bis(p-toluenesulfonyl) sulfodiimide (134 mg, 0.362 mmol) prepared by the method of Wucherpfennig and Kresze, Tet. Lett 1671 (1966). The resulting solution was stirred for 18 hours at room temperature and concentrated in vacuo to give a pale yellow foam (224 mg). A 116 mg portion of the 224 mg was treated directly with 1.3 ml of a solution made from 2.4 g $K_2CO_3$, 12 ml MeOH, and 8 ml $H_2O$. After 14 hours at room temperature, the reaction was diluted with diethyl ether (6 ml) and washed with 2:1 1 N NaOH: brine (1.5 ml), water and brine. The resulting solution was dried with $MgSO_4$ and concentrated in vacuo to give a crystalline solid (54.8 mg). Recrystallization from carbon tetrachloride/hexane gave the desired p-toluenesulfonamide 7 (37 mg, 51%) as colorless crystals: mp 166.5°–168° C.; MS: calcd for $C_{20}H_{28}N_2O_4S$: 392; Found: 392. Anal. calcd for $C_{20}H_{28}N_2O_4S$. 0.25 $H_2O$: C,60.50; H, 7.24; N, 7.06; S,8.08. Found: C, 60.42; H, 7.10; N, 6.98; S, 8.24.

EXAMPLE 7

1,1-dimethylethylhexahydro-5α-(hydroxymethyl)-4β-[ [(4-methylphenyl)sulfonyl]amino]-3aβ,6aβ-cyclopenta[c] pyrrole-2(1H)-carboxylate (Endo alcohol 8)

To a solution of borane in THF (1.82 ml of a 1M solution 1.82 mmol) at 0° C. was added dropwise a solution of 2,3-dimethyl-2-butene (1.82 ml of a 1M solution, 1.82 mmol). The resulting solution was stirred for 2 hours at 0° C. To this solution of thexyl borane at 0° C. was added a solution of p-toluenesulfonamide 7 (230 mg, 0.586 mmol)

from Example 6 in dry THF (3 ml) and the resulting solution was stirred for 20 hours at room temperature. The reaction was cooled to 0° C. and quenched with 10% NaOH (0.91 ml) followed by 30% $H_2O_2$ (0.76 ml) and stirred for ½ hour at 0° C., then 1 hour at room temperature. After concentrating under a stream of nitrogen, water (4 ml) was added and the mixture was extracted with diethyl ether (3×). The combined organic extracts were washed with water (5×) and brine. The solution was dried over $Na_2SO_4$ and concentrated in vacuo to give a residue (297 mg) which was chromatographed on silica gel eluting with ethanol/methylene chloride (1.5/98.5) to give the desired alcohol 8 (92 mg, 38%) as a colorless glass: mp 50°–60° C.; MS: $MH^+$ Calcd for $C_{20}H_{30}N_2O_5S$, 411; Found 411; Calcd for $C_{16}H_{21}N_2O_5S$ (M-Bu$^t$), 353.1171; Found 353.1158. Anal. calc for $C_{20}H_{30}N_2O_5S.¼ H_2O$: C, 57.88; H, 7.41; N, 6.75; S, 7.73. Found: C, 57,89; H, 7.45; N, 6.75; S, 7.71.

EXAMPLE 8

1,1-dimethylethylhexahydro-5α-[[(4-methylphenyl)sulfonyl]oxymethyl]-4β-[[(4-methylphenyl)sulfonyl]amino]-3aβ,6aβ-cyclopenta[c]-pyrrole-2(1H)-carboxylate (tosylate 9)

A solution of alcohol 8 (356 mg, 0.867 mmol) from Example 7 in dry pyridine (6 ml) was treated with p-toluene sulfonyl chloride (496 mg, 2.60 mmol) and the resulting solution was allowed to stand at 0° C. for 45 hours. The reaction mixture was poured onto ice (12 g) and extracted with diethyl ether (3×). The combined organic phases were dried over $MgSO_4$. Concentration in vacuo gave the desired tosylate 9 (470 mg, 96%) as a foam: mp 54°–67° C. Anal. calcd for $C_{27}H_{36}N_2O_7S_2$: C, 57.43; H, 6.42; N, 4.96; S, 11.35. Found: C, 56.72; H, 6.34; N, 4.94; S, 11.18.

EXAMPLE 9

4-methyl-N-(hexahydro-1H-2,5β-methano-3aα,6aα-cyclopenta[c]pyrrole-4α-yl)benzenesulfonamide (p-Toluenesulfonamide Tetracycle 10)

To the tosylate 9 (456 mg, 0.807 mmol) from Example 8 in a flask cooled in an ice bath was added freshly distilled trifluoroacetic acid (2.0 ml). The resulting solution was allowed to warm to room temperature over 20 min. and concentrated in vacuo to give a foam (499 mg) which was dissolved in freshly distilled acetonitrile (16 ml) and treated with Hunig's base (417 mg, 3.23 mmol). The solution was stirred for 20 hours at 45°–50° C. After concentration in vacuo, a concentrated aqueous solution of KOH (13 ml) was added and the mixture was extracted with chloroform (5×). The combined organic extracts were washed with brine and dried over sodium sulfate. Concentration in vacuo gave a residue which was chromatographed on silica gel eluting with ammonia-saturated methanol/chloroform (3/97) to give the desired tetracycle 10 (149 mg, 65%) as a colorless powder: mp 199°14 200° C. (dec.). Anal. calcd for for $C_{15}H_{20}N_2SO_2$: C, 61.62; H, 6.89; N, 9.58; S, 10.96. Found: C, 61.65; H, 6.96; N, 9.53; S, 11.29.

EXAMPLE 10

2-Methoxy-4-acetamido-5-chloro-N-(hexahydro-1H-2,5β-methano-3aα,6aα-cyclopenta[c]pyrrol-4α-yl)benzamide (Benzamide Tetracycle 13)

To a solution of sulfonamide 10 (26 mg, 0.089 mmol) from Example 9 in THF/ammonia (1:1, 6 ml) at −78° C. was added sodium metal (ca. 20 mg). The resulting blue solution was warmed to −33° C. over several minutes and quenched with solid $NH_4Cl$ (160 mg, 3.0 mmol). The mixture was concentrated under a stream of nitrogen leaving a white solid to which was added triethylamine and dimethylformamide (0.8 ml) plus water (1 ml). Concentration in vacuo gave the crude deprotected amino azatetracycle 11, N-(hexahydro-1H-2,5β-methano-3aα, 6aα-cyclopenta[c]pyrrol-4α-yl)amine.

To a solution of benzoic acid derivative 12, 2-methoxy-4-acetamido-5-chlorobenzoic acid, (23.8 mg, 0.098 mmol) in dry DMF (0.2 ml) was added N-methylmorpholine (11 mg, 0.11 mmol). The resulting solution was cooled to 0° C. and isobutylchloroformate (13 mg, 0.098 mmol) was added. After ½ hour at 0°C. the crude deprotected amino azatetracycle 11 was added as a suspension in DMF/triethylamine (1:1, 1.5 ml). The reaction was warmed to 50° C. for 14 hour. After cooling to room temperature, 1N KOH (3.0 ml) was added. The solution was concentrated in vacuo to give a white solid (303 mg) which was dissolved in 2N KOH (1 ml) and extracted with chloroform (5×). The combined extracts were washed with water and brine and dried over $Na_2SO_4$ Concentration under a stream of nitrogen gave an oil (28 mg) which was chromatographed on silica gel. Eluting with methanol (saturated with $NH_3$)/chloroform (3/97) gave the desired benzamide tetracycle 13 as a glass (8.5 mg, 26%). MS calc for $C_{18}H_{22}N_3O_3Cl$: 363.1244; Found: 363.1247.

EXAMPLE 11

2-methoxy-4-amino-5-chloro-N-(hexahydro-1H-2,562-methano-3aα,6aα-cyclopenta[c]-pyrrol-4α-yl)benzamide 14

To a solution of acetamide 13 (8.5 mg, 0.023 mmol) from Example 10 in ethanol (1.5 ml) was added potassium hydroxide (7.7 mg, 0.14 mmol) and the mixture was heated to reflux for 2.5 hours. The resulting solution was cooled and concentrated under a stream of nitrogen to give a residue which was chromatographed on silica gel eluting with ammonia-saturated methanol/chloroform (3/97) to give the desired compound 14 (5.8 mg, 79%) as a glass: MS calculated for $C_{16}H_{20}N_3O_2Cl$ 321.1244; Found 321.1247. $^1H$ NMR (300 MHz, $CDCl_3$) δ8.09 (1H, s), 7.66 (1H, d, J=6 Hz), 6.28 (1H, s), 4.37 (3H, m), 3.88 (3H, s), 3.21 (1H, dd, J=11, 2.6 Hz), 3.05 (1H, dd, J=11, 2.6 Hz), 3.0–2.8 (4H, m), 2.63 (1H, m), 2.56 (1H, m) 2.16 (1H, m), 2.1–1.97 (1H, m), 1.9 (1H, m). $^{13}C$ NMR ($CDCl_3$) 163.3 157.3, 146.5, 133.1, 112.8, 111.8, 97.8, 66.5, 65.0, 62.1, 57.4, 56.2, 45.6, 42.2, 39.2, 37.6 ppm.

EXAMPLE 12

2-methoxy-4-amino-5-chloro-N-(hexahydro-1H-2,5B-methano-3aα,6aα-cyclopenta[c]pyrrol-4α-yl)benzamidehydrochloride 15

To the free base 14 ( 3 mg) from Example 11 dissolved in methanol (0.2 ml) at 5° C. was added HCl/methanol (0.5 ml). The resulting solution was concentrated under a stream of nitrogen, dissolved in water, frozen, and lyophilized to give the desired hydrochloride salt 15 (2.7 mg): MS calcd for $C_{16}H_{20}N_3O_2Cl$, 321.1244, Found, 321.1245. $^1H$ NMR (300 MHz, d4-methanol) δ7.74 (1H, s), 6.54 (1H, s), 4.35 (1H, s), 3.89 (3H, s), 3.71 (1H, dd, J=11, 1.6 Hz), 3.6–3.4 (5H, m), 3.08–2.95 (2H, m), 2.61 (1H, br s), 2.23–2.12 (1H, m), 2.06 (1H, d, J=13 Hz). $^{13}C$ NMR (d4-methanol) δ 166.7, 159.3, 150.0, 132.8, 111.8, 111.4, 98.7, 64.5, 63.5, 61.8, 56.7, 56.0, 43.6, 41.2, 37.5, 36.8 ppm.

EXAMPLE 12A (±)-4-amino-5-chloro-N-(hexahydro-2,5β-methano-1H-3aα,6aα-cyclopenta[c]pyrrol-4α-yl)-2-ethoxybenzamide, hydrochloride

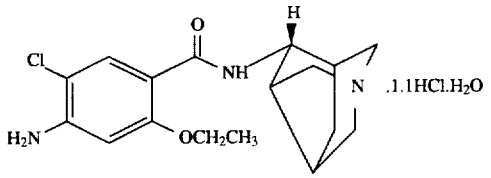

To a solution of 2-ethoxy-4-acetamido-5-chlorobenzoic acid (106 mg, 0.41 mmol) in DMF (1 ml) was added carbonyldiimidazole (67 mg, 0.41 mmol). After stirring for 6h at room temperature a solution of the azatetracycle 11 from Example 18 (57 mg, 0.41 mmol) in DMF (2 ml) was added dropwise and the reaction was stirred for 34 h at room temperature. A solution of potassium carbonate (340 mg) in brine (5 ml) was added and the solution was extracted with chloroform (5×). The combined organic extracts were washed with water and brine, dried over sodium sulfate, and concentrated in vacuo to give a colorless foam (178 mg). This residue was chromatographed on silica gel eluting with ethanol/chloroform/ammonium hydroxide (9.5/90/0.5) to give the desired amide (120 mg, 77%) as a colorless powder. MS calcd for $C_{19}H_{24}N_3O_3Cl$ 377.1506, found 377.1511.

A solution of this acetamide (117 mg) and potassium hydroxide (107 mg, 1.9 mmol) in ethanol (16 ml) was then heated under reflux for 2 h. The solution was then concentrated to a residue which was suspended in 20 ml of water and filtered to give the title compound (89 mg, 86%) as the free base. This amide in methanol (0.5 ml) was treated with HCl/methanol [prepared from acetyl chloride (19 mg, 0.27 mmol) and methanol (0.5 ml)]. The resulting salt was crystallized from methanol/diethyl ether to give the title compound (88 mg) as a colorless powder: mp 263°– 264° C. Anal. calcd for $C_{17}H_{22}N_3O_2Cl..1.1HCl.H_2O$: C, 51.83; H, 6.42; N, 10.67; Cl, 18.90. Found: C, 51.68; H, 6.15; N, 10.69; Cl, 18.61. MS calcd for $C_{17}H_{22}N_3O_2Cl$: 335.1400; found: 335.1414.

EXAMPLE 12B (±)-4-dimethylamino-5-chloro-N-(hexahydro-2,5β-methano-1H-3aα,6aα-cyclopenta[c]pyrrol-4α-yl)-2-methoxybenzamide, hydrochloride

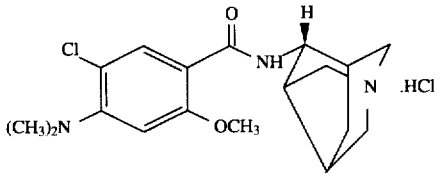

To a solution of 2-methoxy-4-dimethylamino-5-chlorobenzoic acid (67 mg, 0.29 mmol) in DMF (0.5 ml) was added carbonyldiimidazole (47 mg, 0.29 mmol). After stirring for 2h at room temperature a solution of the azatetracycle 11 from Example 18 (40 mg, 0.29 mmol) in DMF (1 ml) was added dropwise and the reaction was stirred for 24 h at room temperature. After the reaction mixture was concentrated in vacuo a concentrated aqueous solution of potassium carbonate was added and the mixture was extracted with chloroform (3×). The combined organic extracts were washed with water (2×) and brine, dried over sodium sulfate, and concentrated in vacuo to give a colorless solid (177 mg). This residue was chromatographed on silica gel eluting with methanol (saturated with NH3)/chloroform (3/97) to give the desired amide 66 mg, 65%) as a colorless powder. This amide in methanol (0.5 ml) was treated with HCl/methanol [prepared from acetyl chloride (13 mg, 0.19 mmol) and methanol (0.5 ml)]. The resulting salt was crystallized from methanol/diethyl ether to give the title compound (64 mg) as a colorless powder: mp 216°–217° C. Anal. calcd for $C_{18}H_{24}N_3O_2Cl,HCl$: C, 55.96; H, 6.62; N, 10.88; Cl, 18.35. Found: C, 55.60; H, 6.35; N, 10.54; Cl, 17.94. MS M+1 calcd for $C_{17}H_{22}N_3O_2Cl$: 350; found: 350.

SCHEME II

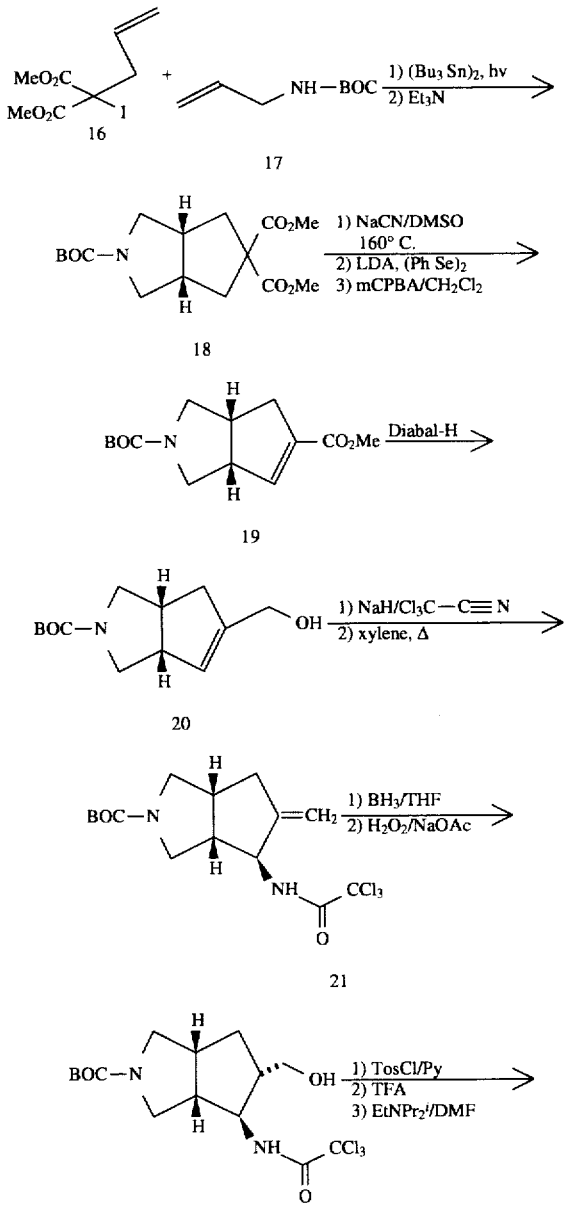

-continued

SCHEME II

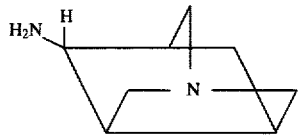

11

The process of Scheme II can be understood with respect to the following discussion. An allyl iodomalonate 16 and N—BOC allylic amine 17 are reacted photolytically to provide azabicyclic malonate 18. The malonate 18 is reacted to produce an unsaturated ester 19. The ester 19 is reduced to provide an allylic alcohol 20 with which its corresponding trichloroimidate is thermally rearranged to give trichloroacetamide 21. The trichloroacetamide 21 is reacted with borane and oxidized with hydrogen peroxide to form the alcohol 22. The alcohol 22 is reacted with p-toluenesulfonyl chloride to produce crude tosylate which is deprotected with trifluoroacetic acid and cyclized in the presence of Hunig's base to yield the tetracycle 11.

Further details of the process shown in Scheme II are exemplified in the following examples 13–18.

EXAMPLE 13

2-(1,1-dimethylethyl)-5,5-dimethyl-3aβ,6aβ-hexahydrocyclopenta[c]pyrrole-2,5,5(1H,4H)-tricarboxylate 18

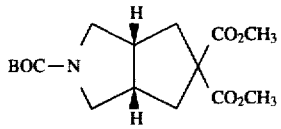

To a solution of 1.27 g (4.26 mmol) of 2-iodo-2-(2'-propen-1-yl)dimethylmalonate (allyl iodomalonate) 16 (ref. Curran, D. P.; Chen, M.-H.; J. Am. Chem. Soc. 1989, vol. 111, p 8872) and 1.34 g (8.52 mmol) of N-butoxycarbamoylallylamine (N-BOC allylic amine) 17 in 10 mL of benzene was added via syringe 0.16 mL of bis(tributyltin). After exposing the clear homogeneous solution to light from a sunlamp (d=8 cm) for 30 min, the light source was removed and 5 mL of triethylamine was added. The solution was heated at reflux for 20 hours at which time the dark brown-red mixture was concentrated under reduced pressure. Flash chromatography on 150 g of silica gel (ethyl acetate:hexane, 1:5 to 1:3) provided 0.61 g of azabicycle 18 as a clear oil. MS: $C_{16}H_{25}NO_6$ $M^+$327. Anal. calcd for $C_{16}H_{25}NO_6$: C, 58.69; H, 7.71; N, 4.28; found: C, 57.87; H, 7.62; N, 4.07.

EXAMPLE 14

2-(1,1-dimethylethyl)-5-methyl-3,3aβ,6aβ-tetrahydrocyclopenta[c]pyrrole-2,5(1H)-dicarboxylate 19

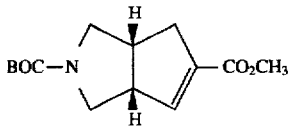

A solution of 8.0 g (24.4 mmol) of azabicycle diester 18 from Example 13 and 1.34 g (26.9 mmol) of sodium cyanide in 100 mL dimethylsulfoxide was heated to 160° C. for 5.5 hours. The mixture was cooled and poured into 4000 mL of water. The solution was extracted with ether (5×2400 mL). The organic extracts were combined, washed with water (4×1000 mL), dried over anhydrous magnesium sulfate, filtered, and concentrated under reduced pressure to provide 4.81 g of diastereomeric esters as a red-brown oil. This product was used without further purification.

To a solution of 3.36 mL (23.9 mmol) of diisopropylamine in 125 mL of tetrahydrofuran at −78° C. was added via syringe 14.4 mL of a 1.55 M solution of n-butyllithium in hexane. After stirring for 5 min, a solution of 4.81 g (17.9 mmol) of diastereomeric esters and 14.3 mL of hexamethylphosphoramide in 75 mL of tetrahydrofuran was added via cannula. The brown solution was stirred at −78° C. for 40 min at which time a solution of 7.2 g (22.3 mmol) of diphenyl diselenide in 50 mL of tetrahydrofuran was added. The resulting red solution was warmed to 0° C. and stirred for 2.5 hours. The solution was poured into 900 mL of a saturated aqueous solution of ammonium chloride and extracted with ether (4×200 mL). The organic extracts were combined, dried over anhydrous magnesium sulfate, filtered, and concentrated under reduced pressure to provide 8.72 g of an orange-red oil. Chromatography on a Waters Prep 500 system (ethyl acetate:hexane, 15:85; flow rate 200 mL/min) afforded 4.74 g of diastereomeric selenides as a yellow oil.

To a solution of 4.74 g (11.2 mmol) of diastereomeric selenides in 175 mL of dichloromethane at −78° C. was added in small portions 2.89 g (16.8 mmol) of m-chloroperbenzoic acid. The suspension was stirred at −78° C. for 2 hours. Dimethyl sulfide (1 ml) was added and the suspension was stirred at −78° C. for an additional hour. After adding 0.5 mL of pyridine, the cold suspension was directly added via cannula to 500 mL of refluxing carbon tetrachloride. The yellow homogeneous solution was refluxed for 2 min, cooled to room temperature in an ice bath, and poured into 800 mL of a saturated aqueous solution of ammonium chloride containing 15 g of potassium carbonate. The mixture was extracted with dichloromethane (4×150 mL). All organic extracts were combined, dried over anhydrous potassium carbonate, filtered, and concentrated under reduced pressure to give 6.77 g of a yellow oil. Chromatography on a Waters Prep 500 system (ethyl acetate:hexane, 15:85 to 25:75; flow rate 200 mL/min) produced 2.02 g of unsaturated ester 19 as an oil. $^1H$ NMR ($CDCl_3$) δ3.76 (3H, s), 6.61 (1H, br s); $^{13}C$ NMR ($CDCl_3$) 136.2, 144.8, 154.0, 165.3 ppm.

EXAMPLE 15

2-(1,1-dimethylethyl)-5-hydroxymethyl-3,3aβ,6,6aβ-tetrahydrocyclopenta[c]pyrrole-2(1H)-carboxylate 20

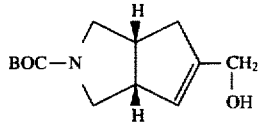

To a solution of 1.96 g (7.32 mmol) of unsaturated ester 19 from Example 14 in 60 mL of dichloromethane at −78° C. was added via syringe 18.3 mL of a 1.0M solution of diisobutylaluminum hydride in dichloromethane. The solution was stirred at −78° C. for 90 minutes. The solution was quenched at −78° C. with 1 mL of methanol and poured into 800 mL of a saturated aqueous solution of Rochelle's salt. After stirring overnight, the mixture was extracted with dichloromethane (4×150 mL). The organic extracts were combined, dried over anhydrous potassium carbonate, filtered, and concentrated under reduced pressure to afford 1.75 g of a pale yellow oil. Flash chromatography on 210 g of silica gel (ethyl acetate:hexane, 1:1) provided 1.5 g of the above alcohol 20 as an oil. $^1$H NMR ($CDCl_3$ ) δ 4.17 (2H, br s), 5.50 (1H, br s); $^{13}$C NMR ($CDCl_3$) 60.5, 126.6, 143.1, 153.7 ppm.

EXAMPLE 16

1,1-dimethylethylhexahydro-5-methylene-4β-[(trichloroacetyl) amino]-3aβ, 6aβ-cyclopenta-[c]pyrrole-2(1H)-carboxylate 21

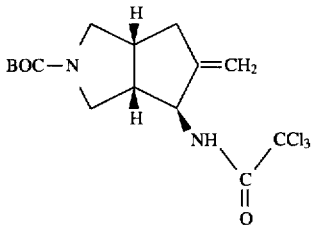

To a suspension of 25 mg (0.63 mmol) of sodium hydride in 11 mL of ether was added a solution of 1.01 g (4.2 mmol) of alcohol 20 from Example 15 in 4 mL of ether. After stirring for 5 min, the pale yellow solution was cooled to 0° C. and treated with 0.44 mL (4.41 mmol) of trichloroacetonitrile. The resulting brown-yellow homogeneous solution was stirred at 0° C. for 15 min, warmed to room temperature, and stirred for 30 min. The mixture was concentrated under reduced pressure. The resulting brown oil was shaken for 1 min in 50 mL of pentane containing 0.06 mL of methanol. The suspension was filtered and concentrated under reduced pressure to give 1.3 g of imidate as a clear oil. IR ($CHCl_3$): 3240 cm$^{-1}$; $^1$H NMR ($CDCl_3$) δ4.85 (2H, br s), 8.12 ppm (1H, br s). A solution of 0.9 g (2.34 mmol) of the imidate in 20 mL of xylene was refluxed for 9 hours. The homogeneous solution was cooled and directly purified on 100 g of silica gel (ethyl acetate:hexane, 1:4) to afford 0.29 g of starting material. Further elution produced 0.17 g of the above trichloroacetamide 21 as a solid. mp 178.0°–179.020 0 C. (ether/dichloromethane). $^1$H NMR ($CDCl_3$) δ4.49 (1H, m), 5.12 ppm (2H, br d).

EXAMPLE 17 hexahydro-5α-(hydroxymethyl)-4β-[(trichloroacetyl)amino]-1H-3aβ,6aβ -cyclopenta[c]pyrrole 22

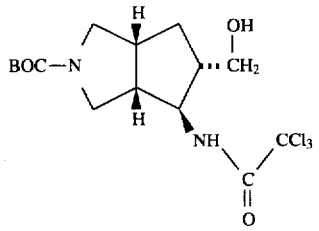

To a solution of 0.16 g (0.41 mmol) of trichloroacetamide 21 from Example 16 in 5 mL of tetrahydrofuran was added via syringe a 1.0M solution of borane/tetrahydrofuran (1.03 ml, 1.03 mmol) complex in tetrahydrofuran. The clear homogeneous solution was stirred for 2 hours at which time it was treated with 10 mL of a 10% aqueous solution of sodium acetate followed by 1.1 mL of a 30% aqueous solution of hydrogen peroxide. After stirring for 3 hours, the solution was extracted with ethyl acetate (4×20 mL). All organic extracts were combined, dried over anhydrous magnesium sulfate, filtered, and concentrated under reduced pressure. Filtration through 50 g of silica gel (ethyl acetate) provided 85 mg of diastereomeric alcohols as an oil. Chromatography on 50 g of silica gel (ethyl acetate:hexane, 2:3) provided 25 mg of the syn diastereomer as an oil. Further elution gave 10 mg of the anti alcohol 22 as an oil. $^1$H NMR ($CDCl_3$) δ3.69 (2H, m), 3.82 ppm (1H, m).

EXAMPLE 18

N-(hexahydro-1H-2,5β-methano-3aα, 6aα-cyclopenta[c]pyrrol-4α-yl)amine 11

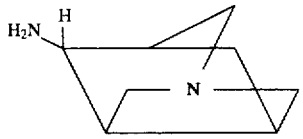

To a solution of 7 mg (0.018 mmol) of anti alcohol from Example 17 in 2 mL of pyridine at 0° C. was added 20 mg (0.105 mmol) of p-toluenesulfonyl chloride. The homogeneous solution was allowed to stand overnight at 5° C. The solution was concentrated under reduced pressure. The solid residue was taken up in 5 mL of water and extracted with ether (2×5 mL). All organic extracts were combined, washed with a saturated aqueous solution of copper (II) sulfate (2×5 mL), washed with 5 mL of brine, dried over anhydrous magnesium sulfate, filtered, and concentrated under reduced pressure to afford 6 mg of crude tosylate as an oil. A solution of the tosylate in 3 mL of trifluoroacetic acid was stirred at 0° C. for 30 min, removed from the ice water bath, and stirred for an additional 30 min. The clear homogeneous solution was concentrated under reduced pressure. The resulting oil was dissolved in 4 mL of dimethylformamide and treated with 0.1 mL of diisopropylethylamine. The solution was stirred for 48 hours at which time it was concentrated under reduced pressure. The residue was taken up in 5 mL of a 10% aqueous solution of potassium carbonate and extracted with chloroform (3×5 mL). All organic extracts were combined, dried over anhydrous potassium carbonate, filtered, and concentrated under reduced pressure. The brown oil was chromatographed on 0.5 g of silica gel (chloroform:methanol:ammonium hydroxide, 85:15:1) to produce 2 mg of the tetracycle 11. $^1$H NMR ($CDCl_3$) δ 2.78 (4H, m), 2.99 (4H, m), 3.32 (1H, br s), 3.50 (2H, br t). $^{13}$C NMR ($CDCl_3$) 37.68, 38.31 41.93, 45.56, 64.73, 65.29, 66.48, 69.83 ppm.

SCHEME III

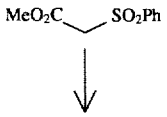

-continued

SCHEME III

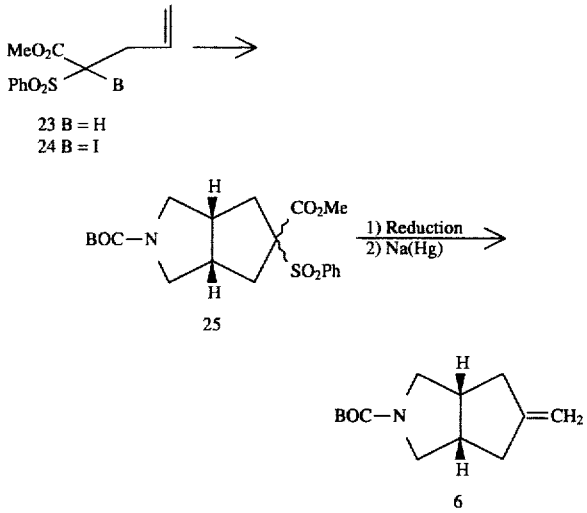

The reaction Scheme III further illustrates a portion of the reaction sequence herein. With respect to reaction Scheme III, methyl phenylsulfonyl acetate is reacted to produce an allylated acetate 23. The allylated acetate is reacted with N-iodosuccinimide to produce an iodinated phenylsulfonyl acetate 24. The iodinated phenylsulfonyl acetate 24 can be reacted to produce the bicyclic compound 25 by reaction with N—BOC allylamine. Reductive elimination of 25 to the bicycloamine 6 offers an alternative approach to this intermediate previously described in Scheme I. The following examples 19–24 further illustrate the reaction sequence shown in Scheme III.

EXAMPLE 19 but-3-en-1-carbomethoxy-1-yl-phenylsulfone 23

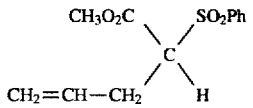

To a suspension of 2.15 g (53.8 mmol) of sodium hydride in 350 mL of tetrahydrofuran at 0° C. was added via cannula a solution of 9.6 g (44.8 mmol) of methyl phenylsulfonyl acetate in 50 mL of tetrahydrofuran. The homogeneous solution was warmed to room temperature and stirred for 15 min. The resulting white suspension was treated with 5.4 g (44.8 mmol) of allyl bromide. After stirring for 20 hours, the mixture was diluted with 100 mL of water and extracted with ethyl acetate (3×200 mL). All organic extracts were combined, dried over anhydrous magnesium sulfate, filtered, and concentrated under reduced pressure to provide 11.5 g of crude product. Chromatography on a Waters Prep 500 system (ethyl acetate:hexane 7:93 to 12:88; flow rate 200 mL/min) afforded 6.86 g of alkylated acetate 23 as an oil. $^1$H NMR ($CDCl_3$) δ2.72 (2H, m), 3.68 (3H, s), 4.02 (1H, dd, J=11.0, 4.0 Hz), 5.13 (2H, m), 5.67 (1H, m), 7.60 (2H, t, J=9.0 Hz), 7.71 (1H, t, J=8.5 Hz), 7.89 (2H, d, J=8.8 Hz). Anal. calcd for $C_{12}H_{14}O_4S$: C, 56.68; H, 5.56; found: C, 56.37; H, 5.54

EXAMPLE 20

2-(1,1-dimethylethyl)-5-methylhexahydro-3aβ, 6aβ-cyclopenta[c]pyrrole-5-(phenylsulfonyl)-2,5(1H,4H)-dicarboxylate 25

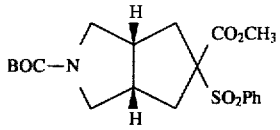

To a suspension of 50 mg (1.23 mmol) of sodium hydride in 25 mL of tetrahydrofuran was added 0.285 g (1.12 mmol) of the sulfone 23 from Example 19. After stirring for 30 min, the clear mixture was treated via cannula with a solution of 0.25 g (1.12 mmol) of N-iodosuccinimide in 10 mL of tetrahydrofuran. The resulting suspension was stirred in the dark for 1 hour at which time it was directly purified on 75 g of silica gel (ether) to provide 0.38 g of labile iodosulfonyl acetate 24 as an orange brown oil. To a solution of 0.38 g (0.92 mmol) of iodosulfonyl acetate 24 and 0.29 g (1.85 mmol) of N—BOC allylamine in 3 mL of benzene was added via syringe 0.054 mL (0.14 mmol) of bis(tributyltin). The clear homogeneous solution was exposed to light from a sunlamp (d=8 cm) for 30 min at which time the light source was removed and 1.5 mL of triethylamine was added. The resulting red-brown homogeneous solution was heated to reflux for 14 hours. The suspension was concentrated under reduced pressure and filtered through 50 g of silica gel (ethyl acetate:hexane, 1:1) to provide a brown oil. Medium pressure liquid chromatography (ethyl acetate:hexane, 1:2; flow rate 8 mL/min; 15×1000 mm column) afforded 0.17 g of bicycle 25 as an oil. $^{13}$C NMR ($CDCl_3$) 27.2, 35.1, 36.3, 40.4, 40.7, 48.7, 49.5, 52.1, 78.5, 79.0, 127.9, 128.4, 133.2, 136.0, 153.8, 167.5 ppm. MS for $C_{20}H_{27}NO_6S$: $M^{+1}$ 410.

EXAMPLE 21

2-(1,1-dimethylethyl)-5-(phenylsulfonyl)-5-(formyl)-hexahydro-3-aβ, 6aβ-cyclopenta[c]pyrrole-2 (1H)-carboxylate 26

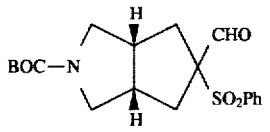

To a solution of 3.6 g (8.84 mmol) of bicycle 25 from Example 20 in 100 mL of dichloromethane at −78° C. was added via syringe 20.6 mL (20.6 mmol) of a 1.0M solution of diisobutylaluminum hydride in dichloromethane. After stirring for 1 hour at −78° C., the solution was quenched with 3 mL of methanol and poured into 800 mL of a saturated aqueous solution of Rochelle's salt. The mixture was stirred overnight and extracted with chloroform (4×500 mL). All organic extracts were combined, dried over anhydrous potassium carbonate, filtered, and concentrated under reduced pressure to provide 3.1 g of the above aldehyde 26 as an oil $^1$H NMR ($CDCl_3$) δ9.72 (1H, s).

EXAMPLE 22

2-(1,1-dimethyl)-5-(phenylsulfonyl)-5-(hydroxymethyl)-hexahydro-3aβ,6aβ-cyclopenta[c] pyrrole-2(1H)-carboxylate 27

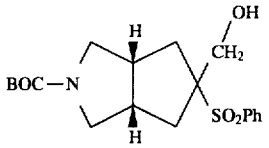

To a solution of 3.1 g (8.06 mmol) of aldehyde 26 from Example 21 in 35 mL of tetrahydrofuran at 0° C. was added via syringe 6.05 mL (12.1 mmol) of a 2.0M solution of lithium borohydride in tetrahydrofuran. After stirring at 0° C. for 1 hour, the clear homogeneous solution was carefully quenched with 15 mL of a 2% aqueous solution of hydrochloric acid and poured into 50 mL of water. The mixture was extracted with ether (3×100 mL). All organic extracts were combined, dried over anhydrous magnesium sulfate, filtered, and concentrated under reduced pressure to afford 3.09 g of a solid. Recrystallization from ether afforded analytically pure alcohol 27, mp 126.0°–127.0°C. Anal. calcd for $C_{19}H_{27}NO_5S$: C, 59.82; H, 7.15; N, 3.67; found: C, 59.58; H, 7.14; N, 3.58.

EXAMPLE 23

2-(1,1-dimethyl)-5-(phenylsulfonyl)-5-(acetoxymethyl)-hexahydro-3aβ,6aβ-cyclopenta[c] pyrrole-2(1H)-carboxylate 28

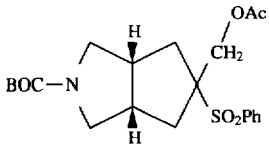

To a solution of 3.27 g (8.57 mmol) of alcohol 27 from Example 22 and 2.1 mL (25.7 mmol) of pyridine in 40 mL of tetrahydrofuran was added 0.9 mL (12.9 mmol) of acetyl chloride. The suspension was stirred for 18 hours at which time it was concentrated under reduced pressure. The solid was dissolved in 50 mL of water and extracted with ether (4×50 mL). All organic extracts were combined, washed with a saturated aqueous solution of copper(II) sulfate (2×50 mL), washed with 50 mL of brine, dried over anhydrous magnesium sulfate, filtered, and concentrated under reduced pressure. Chromatography on 100 g of silica gel (ethyl acetate:hexane, 2:3) provided 3.24 g of the above acetate 28 as a foam. $^1$H NMR ($CDCl_3$) δ1.64 (9H, s), 4.16 (2H, s), 7.47 (2H, t, J=8 Hz), 7.58 (1H, t, J=7.5 Hz), 7.78 (2H, d, J=7.5 Hz). Anal. calcd for $C_{21}H_{29}NO_6S$: C, 59.55; H, 6.92; N, 3.31; found: C, 58.94; H, 7.01; N, 3.09.

EXAMPLE 24 cis-1,1-dimethylethylhexahydro-5-methylenecyclopenta[c] pyrrole-2(1H)-carboxylate 6

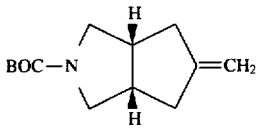

To a solution of 0.34 g (0.8 mmol) of acetate 28 from Example 23 in 21 mL of tetrahydrofuran and 7 mL of methanol at 20° C. was added 17.7 g of pulverized 2.5% sodium amalgam. The mixture was stirred at −20° C. for 3 hours, warmed to 10° C. and diluted with 75 mL of water The mixture was decanted and filtered. The filtrate was extracted with ether (4×50 mL). The organic extracts were combined, dried over anhydrous magnesium sulfate, filtered, and concentrated under reduced pressure. Chromatography on 20 g of silica gel (ethyl acetate:hexane; 1:4) provided 0.1 g of the above alkene 6 as an oil. This product was identical in all aspects to alkene 6 of Example 5 synthesized by the alternate scheme.

The following reaction Scheme IV illustrates another method for producing tetracyclic benzamides. In the reaction sequence shown in Scheme IV a compound 8 is oxidized with pyridinium dichromate (PDC) to produce the compound 23. The compound 23 is reacted to produce compound 24. Compound 24 is reacted to produce the tetracycle 25 which can be reductively cleaved to produce the tetracycle 26. The tetracyle 26 can be reacted with a benzamide 12 to produce the tetracycle benzamide 27 which can be deprotected with base followed by treatment with HCl to produce the benzamide tetracycle hydrochloride 28. The Example 25 following the reaction Scheme IV is illustrative of the reaction sequence shown in the reaction Scheme IV.

SCHEME IV

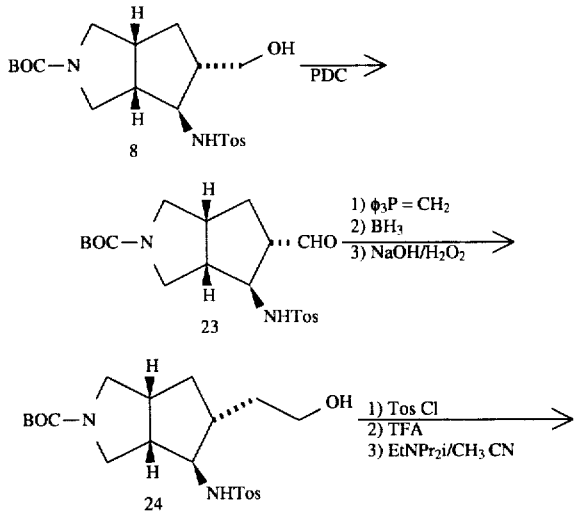

-continued

SCHEME IV

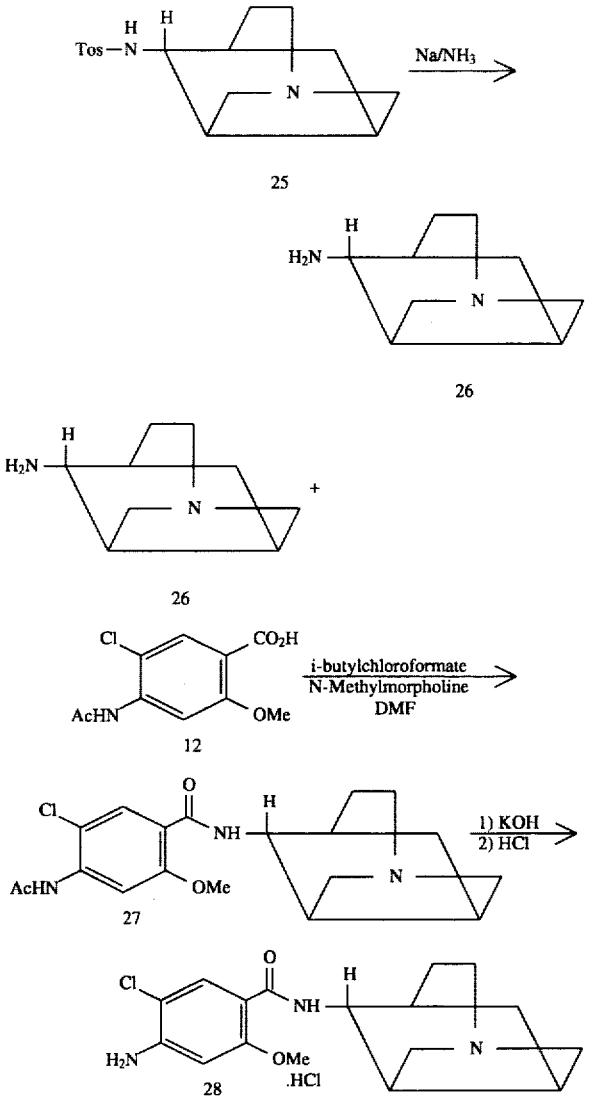

EXAMPLE 25

4-methyl-N-(hexahydro-1H-2,5β-ethano-3aα,6aα-cyclopenta[c]pyrrole- 4α-yl)benzenesulfonamide 26

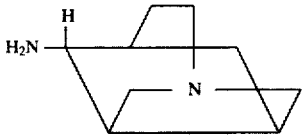

The previously described alcohol 8 is oxidized with pyridinium chlorochromate to afford the aldehyde 23. Wittig olefination ($Ph_3PCH_2$) of the aldehyde 23, followed by hydroboration/oxidation ($BH_3$/THF; then $H_2O_2$/NaOH) gives the homologated alcohol 24. Tosylation, deprotection, and closure performed in a manner as set forth in Examples 8 and 9 yields the desired compound 25 Reductive removal ($Na/NH_3$) of the tosyl protecting group yields the tetracycle 26.

The indoles, benzofurans, benzothiophenes, indenes, benzimidazoles and indazoles can be formed by the following reaction sequence wherein m can be 1 or 2 depending upon which tetracycle is to be formed.

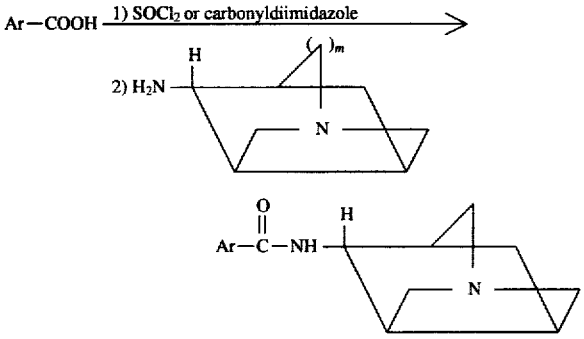

EXAMPLE 26

(±)-N-(hexahydro-1H-2,5β-methanol-3aα,6aα-cyclopenta[c]pyrrol-4α-yl)-1H-indole-3-carboxamide, monohydrochloride

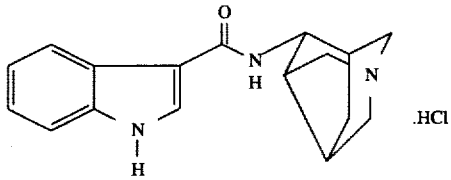

To a solution of indole-3-carboxylic acid (64 mg, 0.40 mmol) in DMF (1 ml) was added carbonyldiimidazole (64 mg, 0.40 mmol). After stirring for 4.5h at room temperature a solution of azatetracycle 11 (52 mg, 0.38 mmol) in DMF (2 ml) was added dropwise and the reaction was stirred for 40h at room temperature. Concentration in vacuo gave a residue which was extracted with ethyl acetate (4×) after the addition of 3 ml of 1N KOH. The combined organic extracts were washed with water (3×) and brine and then dried with $Na_2SO_4$. Concentration in vacuo gave a colorless solid (95 mg) which was chromatographed on silica gel eluting with methanol/chloroform/ammonium hydroxide (9.5/90/0.5) to give the desired amide (40 mg, 38%) as a colorless powder.

This amide in methanol (0.5 ml) was treated with HCl/methanol [prepared from acetyl chloride (9.5 mg, 0.12 mmol) and methanol (0.5 ml)]. The resulting salt was crystallized from methanol/diethyl ether to give the title compound (28 mg) as a colorless powder: mp 324°–325° C. (dec). Anal. calcd for $C_{17}H_{19}N_3O.HCl.¼H_2O$: C,63.35; H, 6.41; N, 13.04. found: C, 63.65; H, 6.41; N, 12.88. MS calcd for $C_{17}H_{19}N_3O$: 281.1528; found: 281.1528.

EXAMPLE 27

(±)-N-(hexahydro-1H-2,5β-methano-3aα,6aα -cyclopenta[c]pyrrol-4α-yl)-1-methyl-1H-indazole-3 -carboxamide, hydrochloride

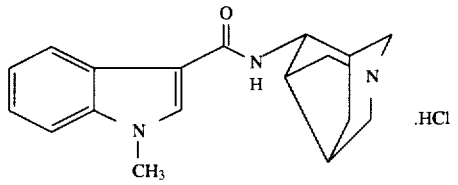

To a solution of N-methylindazole-3-carboxylic acid (83 mg, 0.47 mmol; prepared by the method of Fludzinski (J. Med. Chem., Vol. 30, 1535, 1987) in DMF (1 ml) was added carbonyldiimidazole (76 mg, 0.47 mmol). After stirring for 3h at room temperature a solution of azatetracycle 11 (65 mg, 0.47 mmol) in DMF (2 ml) was added dropwise. The resulting suspension was stirred for 20h at room temperature, then heated to 65° C. for 1.5h. The reaction mixture was then concentrated under a stream of nitrogen. To the residue was added 1N KOH (5ml) followed by extractions with chloroform (5×). The combined organic extracts were washed with water (4×) and brine, dried ($Na_2SO_4$), and concentrated in vacuo to give a pale yellow foam (145 mg).

Purification on silica gel eluting with methanol (saturated with ammonia)/chloroform (3/97) gave the desired amide (89 mg, 64%) free base as a colorless powder: mp 186.5°–187° C. To a solution of this material (85.3 mg, 0.288 mmol) in methanol (0.5 ml) was added a solution of HCl in methanol [made from acetyl chloride (25 mg, 0.32 mmol) and methanol (0.5 ml)]. Crystallization from methanol/diethyl ether gave the title compound (92.5 mg) as a colorless powder: mp 141°–149° C. Anal calcd for $C_{17}H_{20}N_4O.1.1HCl.1.1H_2O$: C, 57.31; H, 6.59; N, 15.73; Cl, 10.95. Found: C, 57.35; H, 6.59; N, 15.48; Cl, 10.81. MS calcd for $C_{17}H_{20}N_4O$ 296.1640; found: 296.1628.

The method for the synthesis of compounds wherein Ar is

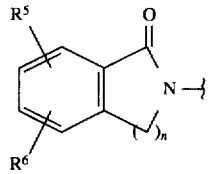

Is shown by the following reaction sequence.

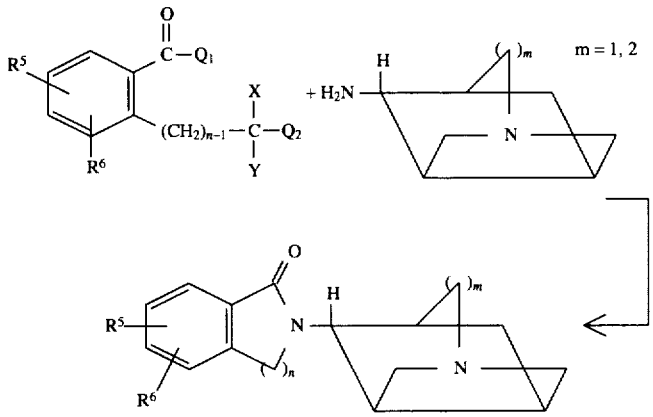

The aromatic moiety can be synthesized in the matter disclosed in Australian patent application AU8207867 (beginning at about page 14 thereof). The coupling of the tetracyclic moiety to the aromatic moiety can be performed in the manner as taught in the Australian patent application AU 8207867.

For the synthesis of compounds wherein the aromatic moiety has the following structure

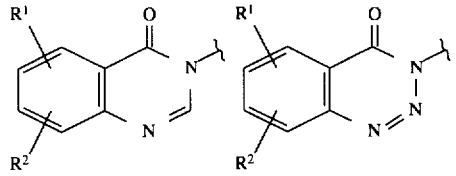

The method disclosed in European patent application 88310208.9 having publication no. 0315390A2 beginning at about page 6 thereof for making the aromatic moiety and bonding a cyclic moiety to such aromatic moiety can be used but using the tetracyclic moieties herein described.

A synthesis of compounds wherein the aromatic moiety has the following structure as is described in Australian Patent 8767121

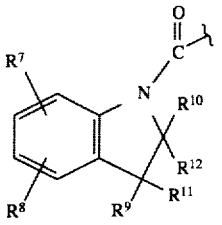

can be reacted in the reaction sequence using the techniques described in the Australian Patent to bond the cyclic moiety therein but using the tetracyclic moieties described herein.

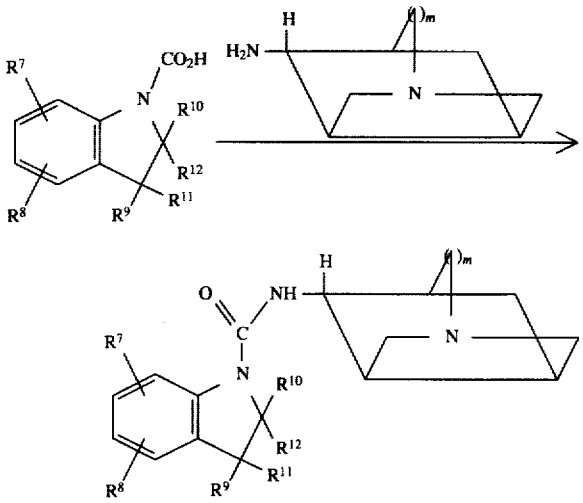

The method for the coupling procedure is shown in Australian patent application 8767121 beginning at about page 8 thereof.

The azatetracyclic alcohols 32 and 35 are prepared according to Scheme V. Thus treatment of the previously described olefin 6 with selenium dioxide, followed by alcohol protection gives the silylated ether 29. Hydroboration (thexyl borane) of the ether 29 gives the alcohol 30. Treatment of the alcohol 30 with tosyl chloride, followed by trifluoroacetic acid and Hunig's base affords the protected tetracycle 31. Removal of the silyl protecting group ($Bu_4NF$/THF) gives the desired azatetracyclic alcohol 32.

Alternatively, treatment of compound 30 with pyridinium chlorochromate (PCC), followed by Wittig olefination ($Ph_3PCH_2$) and hydroboration ($BH_3$/THF) gives the homologated alcohol 33. Treatment of the alcohol 33 with tosyl chloride, followed by trifluoroacetic acid and Hunig's base affords the protected tetracycle 34. Removal of the silyl protecting group ($Bu_4NF$/THF) gives the desired azatetracyclic alcohol 35.

SCHEME V

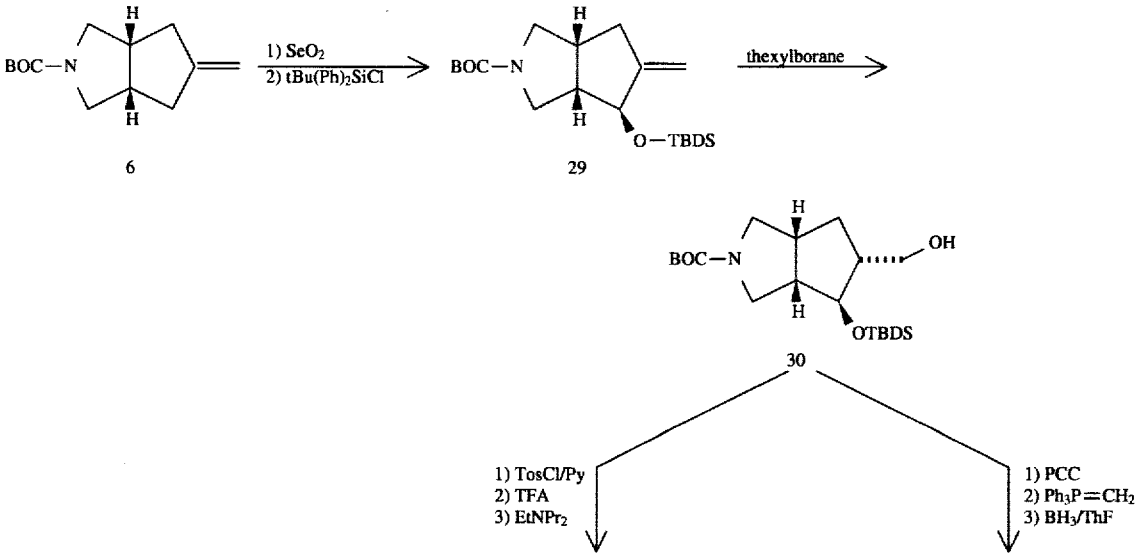

-continued

SCHEME V

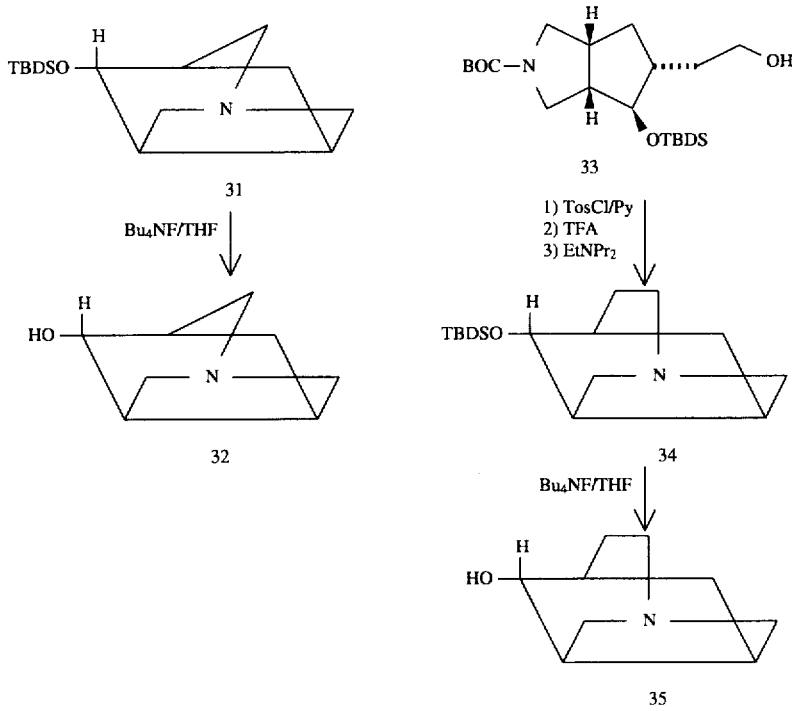

The compounds of formula I wherein p is one, A is NH and B is NH or O can be prepared in accordance with the procedures described in U.S. Pat. No. 4,797,387 the entire disclosure of which is incorporated herein by this reference. As shown in the following reaction Scheme VI a compound 36 is reacted with H—BD (compound 11, 26, 32, or 35) to give the desired compound of formula I. When A' is H, then B' is $COL_1$ wherein $L_1$ is a group displaceable by H—BD. Examples of $L_1$ include chloro, bromo, $C_{1-4}$ alkoxy, PhO—, or $Cl_3CO$—. The reactions are preferably performed in an inert nonhydroxylic solvent such as benzene, methylene chloride, toluene, diethyl ether, tetrahydrofuran (THF), or dimethylformamide (DMF). It is also preferable to perform the reaction in the presence of an acid acceptor such as triethylamine, pyridine, calcium carbonate, sodium carbonate, or potassium carbonate. Optionally, A' and B' together can be =C=O, wherein H—BD is reacted with the compound 29 in an inert solvent as described above.

Alternatively, the compounds of formula I wherein p is 1, A is NH and B is NH or 0 can be prepared by treating $ArNH_2$ (37) with compounds of formula 38 ( an isocyanate or activated carbonyl derivative of azatetracycles 11, 26, 32 or 35). $L_1$ is as described above. The reaction is performed in a nonhydroxylic solvent such as methylene chloride, THF, or DMF and preferably in the presence of an acid acceptor as identified above.

Scheme VI

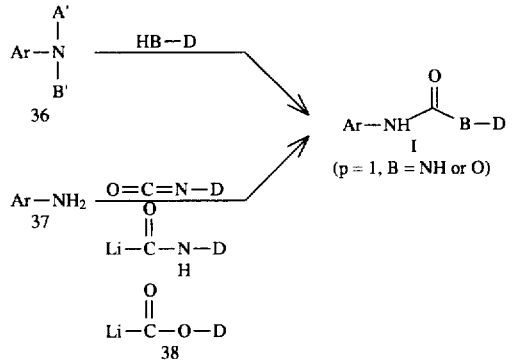

The compounds herein have been found to be useful for treating gastrointestinal motility disorders in mammals. Their usefulness has been shown by their demonstrated prokinetic activity. Prokinetic activity of a compound can be determined by measuring the enhancement of gastric emptying of a meal in a rat model to which the compound has been administered. This method for determining prokinetic activity of a compound has been described by Droppleman, et al, J. Pharmacol. and Methods 4: 227–230 (1980).

The compounds herein exhibit 5-HT3 antagonism. 5-HT3 antagonism can be determined in a model of emesis induced by the chemotherapeutic agent cisplatin as described herein.

Antiemetic Activity

Antiemetic activity of test compound against cisplatin was determined in beagle dogs. Dogs are pretreated I.V. with a test compound dissolved in DMSO thirty minutes before administration of cisplatin 3 mg/kg.i.v. with a second dose of compounds given i.v. two hours after cisplatin administration. Emetic episodes are counted for 5 hours following cisplatin administration. The latency for first emesis and the number of emetic episodes for test compounds are compared with results for control treatment (vehicle).

Percent inhibition of emesis for each animal is determined by the following formula:

$$\frac{\text{No. of emetic episodes per treated dog}}{\text{mean no. of emetic episodes all vehicle-treated dogs}} - 1.0 \times 100\% = \%$$

A mean inhibitory dose ($ID_{50}$) which results in 50% inhibition of the number of emetic episodes is determined.

Antiemetic activity of a representative compound was demonstrated as shown by the results in the following Table II which includes results for BRL 24924, cisapride and ICS 205–930.

TABLE II

| COMPOUND | $ID_{50}$ (mg/kg iv) |
|---|---|
| Example 12 | 0.03 |
| Example 27 | 0.10 (72% inhibition) |
| BRL-24924 | 0.10 |
| Cisapride | 0.6 |
| ICS 205-930 | 0.01 |

Rat Gastric Emptying Protocol

A test meal for measuring gastric emptying in rats was prepared. Ten grams of methylcellulose (2% solution= 15 centipoises; Aldrich Chemical Company, Milwaukee, Wis.) was added to 200ml of cold water and mixed at 20,000 rpm in a Waring blender to insure dispersion and hydration of the methylcellulose. In addition, two beef bouillon cubes (Wyler's, Columbus, Ohio) dissolved in 100ml of warm water was added to the mixture, followed by 16g of casein (Hammersten, Schwartz/Mann, Orangeburg, N.Y.), 8g of powdered confectioners sugar and 8g of cornstarch. The ingredients were mixed for two minutes at 20,000 rpm and the resultant test meal was refrigerated for 48 hours to allow trapped air to escape. Male Charles River Rats, Crl: COBS, CD (SD) BR Strain, 180–200g body weight, were used in groups of six animals. The animals were food deprived for 24 hours prior to the experiment with access to water ad libitum. The compounds to be evaluated were prepared in a 0.5% aqueous methylcellulose solution. If insoluble, the mixture was homogenized for two minutes at 5500 rpm using a Try-R-Stir-R. The compounds were injected intraperitoneally at a volume of 5ml/kg, 30 minutes before the test meal, (3.0ml/rat i.g.). Control animals received only the vehicle. Sixty minutes after the test meal, the rats were sacrificed by cervical dislocation. The stomachs were removed intact and weighed. The stomachs were kept opened, gently rinsed with tap water, blotted dry with paper towelling, and the empty stomach weighed. The difference between the weight of the full and empty stomach is indicative of the amount of meal remaining in the stomach. The amount of meal remaining in the stomach was subtracted from the weight of 3ml of the test meal to determine the amount of food emptied from the stomach during the test. Weight of the test meal was determined by weighing three samples (3ml) at the beginning and three samples at the end of each experiment and calculating the mean. The mean and standard error of the amount of meal emptied were calculated.

The results of following the protocol and comparing representative compounds herein to known prokinetic agents, metoclopramide and cisapride, are shown in Table III.

TABLE III

| COMPOUND | DOSE (mg/kg ip) | % INCREASE IN GASTRIC EMPTYING |
|---|---|---|
| EXAMPLE 12 | 0.001 | −5.8 |
| | 0.01 | 2.0 |
| | 0.03 | 16.4 |
| | 0.1 | 31.3 |
| | 0.3 | 32.1 |
| | 1.0 | 45.3 |
| BRL-24924 | 1.0 | 29.8 |
| | 3.0 | 34.2 |
| | 10.0 | 35.2 |
| METOCLOPRAMIDE | 1.0 | 2.6 |
| | 3.0 | 11.2 |
| | 10.0 | 34.1 |
| CISAPRIDE | 1.0 | 9.8 |
| | 3.0 | 15.4 |
| | 10.0 | 25.0 |
| ZACOPRIDE | 0.3 | 1.4 |
| | 1.0 | 11.8 |
| | 3.0 | 9.3 |
| | 10.0 | 18.5 |
| | 30.0 | 6.3 |

We claim:

1. A compound of the formula

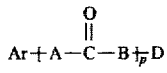

wherein D is

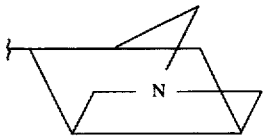

or

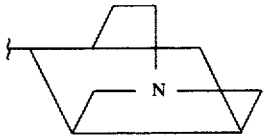

wherein B is NH or O;
wherein A is NH or a bond;
wherein p is 1 or 0; and
when p is 1, Ar is

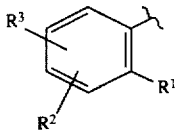

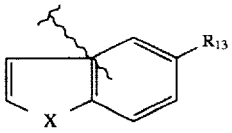

-continued

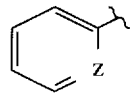

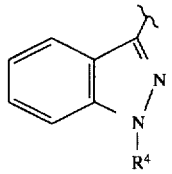

and when p is 0, Ar is

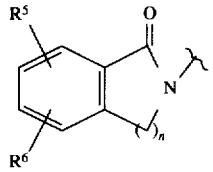

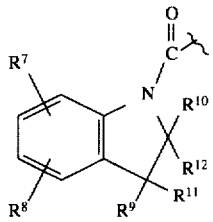

wherein X is O,S,N($R^4$) or $CH_2$;
wherein Y is N or CH;
wherein n is 1 or 2;
wherein Z is

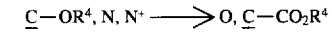

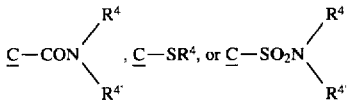

wherein $R^1$ is alkoxy of 1 to 6 carbon atoms;

wherein $R^2$ and $R^3$ are the same or different and is hydrogen, halogen, $CF_3$, hydroxyl, $C_{1-2}$ alkoxy, $C_{2-7}$ acyl, amino, amino substituted by one or two $C_{1-6}$ alkyl groups, $C_{2-7}$ acyl amino, amino carbonyl, or amino sulfone optionally substituted by one or two $C_{1-6}$ alkyl groups, $C_{1-6}$ alkyl sulfone or nitro groups;

wherein $R^4$ and $R^{4'}$ can be the same or different and is hydrogen, alkyl or arylalkyl; wherein $R^5$ and $R^6$ is the same or different and is hydrogen, halogen, $CF_3$, $C_{1-6}$ alkyl, $C_{1-7}$ acyl, $C_{1-7}$ acylamino, or amino, amino carbonyl or amino sulfonyl, optionally substituted by one or two $C_{1-6}$ alkyl or $C_{3-8}$ cycloalkyl groups, or by $C_{4-5}$ polymethylene or biphenyl, $C_{1-6}$ alkylsulfonyl, $C_{1-6}$ alkylsulfinyl, $C_{1-6}$ alkoxy, $C_{1-6}$ alkylthio, hydroxy or nitro or when $R^5$ and $R^6$ are taken together are methylenedioxy or ethylenedioxy;

wherein $R^9$ and $R^{10}$ can be the same or different and is hydrogen, $C_{1-6}$ alkyl, $C_{2-6}$ alkenyl, $C_{1-4}$ alkynyl or together are $C_{2-4}$ polymethylene;

wherein $R^7$ and $R^8$ are the same or different and is hydrogen, halogen, $CF_3$, $C_{1-6}$ alkyl, $C_{1-6}$ alkoxy, $C_{1-6}$ alkylthio, $C_{1-7}$ acyl, $C_{1-7}$ acylamino, $C_{1-6}$ alkylsulfonylamino, N-($C_{1-6}$ alkylsulfonyl)-N-$C_{1-4}$ alkylamino, $C_{1-6}$ alkylsulfinyl, hydroxy, nitro or amino, aminocarbonyl, aminosulfonyl, aminosulfonylamino or N-(aminosulfonyl)-$C_{1-4}$ alkylamino optionally N'-substituted by one or two groups selected from $C_{1-6}$ alkyl, $C_{3-8}$ cycloalkyl, phenyl, or phenyl $C_{1-4}$ alkyl groups or optionally N'-disubstituted by $C_{4-5}$ polymethylene; and wherein $R^{11}$ and $R^{12}$ can be the same or different and is hydrogen or $C_{1-4}$ alkyl or taken together are a covalent bond; and wherein $R^{13}$ is H, halogen or $OR^4$.

2. A compound as recited in claim 1 wherein D is

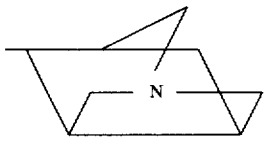

3. A compound as recited in claim 2 wherein p is 1.

4. A compound as recited in claim 3 wherein B is NH.

5. A compound as recited in claim 4 wherein A is a covalent bond.

6. A compound as recited in claim 5 wherein Ar is

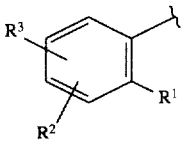

7. A compound as recited in claim 6 wherein $R_1$ is methoxy;

$R_2$ is amino; and $R_3$ is chloro.

8. A compound as recited in claim 7 having the structure

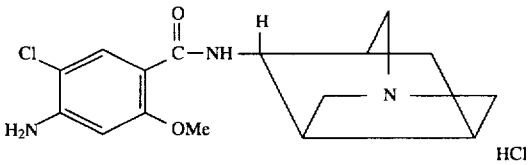

9. A compound as recited in claim 5 wherein Ar is

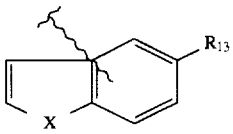

10. A compound as recited in claim 9 wherein X is NH.

11. A compound as recited in claim 5 wherein Ar is

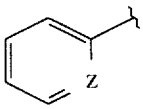

12. A compound as recited in claim 5 wherein Ar is

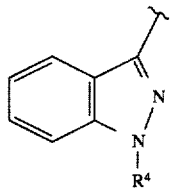

13. A compound as recited in claim 12 wherein $R^4$ is a methyl group.

14. A compound as recited in claim 5 wherein Ar is

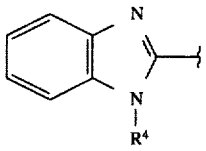

15. A compound as recited in claim 4 wherein A is NH.

16. A compound as recited in claim 15 wherein Ar is

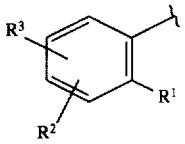

17. A compound as recited in claim 15 wherein Ar is

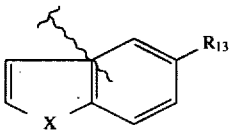

18. A compound as recited in claim 15 wherein Ar is

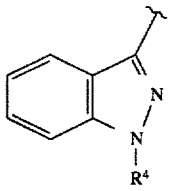

19. A compound as recited in claim 15 wherein Ar is

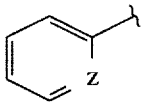

20. A compound as recited in claim 15 wherein Ar is

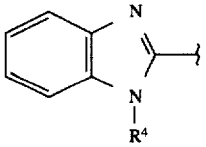

21. A compound as recited in claim 3 wherein B is 0.

22. A compound as recited in claim 2 wherein p is 0.

23. A compound as recited in claim 22 wherein Ar is

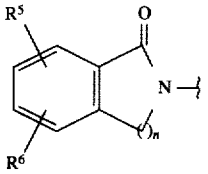

24. A compound as recited in claim 22 wherein Ar is

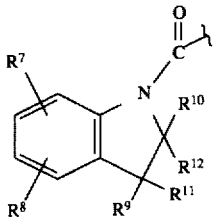

25. A compound as recited in claim 1 wherein D is

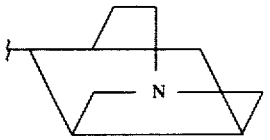

26. A compound as recited in claim 25 wherein p is 1.

27. A compound as recited in claim 26 wherein B is NH.

28. A compound as recited in claim 27 wherein A is a covalent bond.

29. A compound as recited in claim 28 wherein Ar is

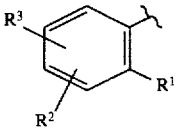

30. A compound as recited in claim 29 wherein $R_1$ is methoxy;

$R_2$ is amino; and $R_3$ is chloro.

31. A compound as recited in claim 28 wherein Ar is

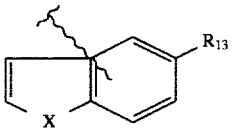

32. A compound as recited in claim 28 wherein Ar is

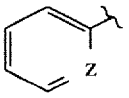

33. A compound as recited in claim 28 wherein Ar is

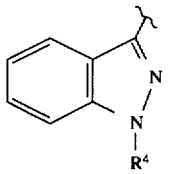

34. A compound as recited in claim 28 wherein Ar is

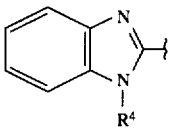

35. A compound as recited in claim 27 wherein A is NH.

36.

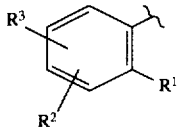

37. A compound as recited in claim 35 wherein Ar is

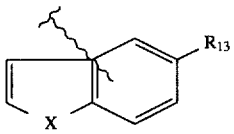

38. A compound as recited in claim 35 wherein Ar is

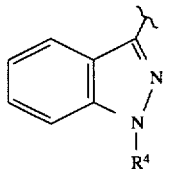

39. A compound as recited in claim 35 wherein Ar is

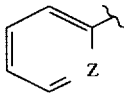

40. A compound as recited in claim 35 wherein Ar is

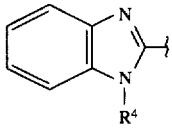

41. A compound as recited in claim 26 wherein B is 0.

42. A compound as recited in claim 25 wherein p is 0.

43. A compound as recited in claim 42 wherein Ar is

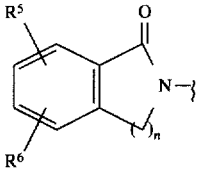

44. A compound as recited in claim 42 wherein Ar is

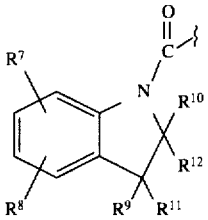

45. A pharmaceutical composition comprising therapeutically or prophylactically effective amount of a compound of claim 1 of the formula $$Ar+A-\overset{O}{\overset{\|}{C}}-B\underset{p}{+}D$$

and a pharmaceutical carrier.

46. A pharmaceutical composition as recited in claim 45 wherein D is

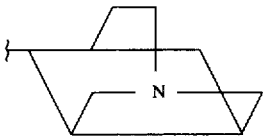

47. A pharmaceutical composition as recited in claim 45 wherein D is

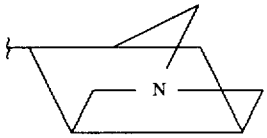

48. A method of treating gastrointestinal motility disorders comprising administering to a patient in need of such treatment, a therapeutically effective amount of a compound according to claim 2 and a pharmaceutically acceptable carrier.

49. A method of treating gastrointestinal motility disorders comprising administering to a patient in need of such treatment, a therapeutically effective amount of a compound according to claim 25 and a pharmaceutically acceptable carrier.

50. A method of preventing emesis or ileus comprising administering to a patient in need of such treatment, a therapeutically effective amount of a compound according to claim 2 in a pharmaceutically acceptable carrier.

51. A method for preventing emesis or ileus comprising administering to a patient in need of such treatment, a therapeutically effective amount of a compound according to claim 25 in a pharmaceutically acceptable carrier.

52. A method of treating emesis, anxiety, pain, schizophrenia, depression, substance abuse, memory impairment, or related diseases having a serotonergic etiology benefiting from use of a serotonergic 5-$HT_3$ antagonist comprising administering to a patient in need of such treatment, a therapeutically effective amount of a compound according to claim 2 and a pharmaceutically acceptable carrier.

* * * * *